United States Patent [19]

Ma et al.

[11] Patent Number: 5,571,850

[45] Date of Patent: Nov. 5, 1996

[54] AQUEOUS DISPERSIONS CONTAINING CYCLOPOLYMER DISPERSANTS

[75] Inventors: Sheau-Hwa Ma, Chadds Ford, Pa.; San Hoa Thang, Clayton, Australia; Ezio Rizzardo, Wheelers Hill, Australia; Graeme Moad, Kallista, Australia

[73] Assignee: E. I. Du Pont de Nemours and Company, Wilmington, Del.

[21] Appl. No.: 586,852

[22] PCT Filed: Jul. 29, 1994

[86] PCT No.: PCT/US94/08645

§ 371 Date: Jan. 25, 1996

§ 102(e) Date: Jan. 25, 1996

[87] PCT Pub. No.: WO95/04109

PCT Pub. Date: Feb. 9, 1995

[30] Foreign Application Priority Data

Jul. 30, 1993 [AU] Australia .................... PM 0280/93

[51] Int. Cl.$^6$ ................. C09D 11/02; C08L 9/00
[52] U.S. Cl. ............ 523/160; 524/499; 524/571; 106/20 D; 106/23 C
[58] Field of Search .................... 523/160, 161; 524/499, 571; 106/20 D, 23 C

[56] References Cited

U.S. PATENT DOCUMENTS

| | | | |
|---|---|---|---|
| 4,597,794 | 7/1986 | Ohta et al. | 106/20 |
| 5,085,698 | 2/1992 | Ma et al. | 106/20 |
| 5,510,415 | 4/1996 | Zahrobsky et al. | 106/20 D |

*Primary Examiner*—Tae Yoon

[57] ABSTRACT

Aqueous dispersions which are particularly well suited for use as aqueous jet ink compositions having an aqueous carrier medium which comprises water or a mixture of water and at least one organic solvent, a particulate solid, preferably a pigment, and a cyclopolymer dispersant.

9 Claims, No Drawings

AQUEOUS DISPERSIONS CONTAINING CYCLOPOLYMER DISPERSANTS

FIELD OF THE INVENTION

This invention relates to aqueous dispersions having excellent stability. In a preferred embodiment, this invention relates to aqueous pigmented inks for ink jet printers wherein the pigment dispersant is a cyclopolymer.

BACKGROUND OF THE INVENTION

Water-based pigment dispersions are well known in the art, and have been used commercially for applying films, such as paints, to various substrates. The pigment dispersion is generally stabilized by either a non-ionic or ionic technique. When using the non-ionic technique, the pigment particles are stabilized by a polymer that has a water-soluble, hydrophilic section that extends into the water and provides entropic or steric stabilization. Representative polymers useful for this purpose include polyvinyl alcohol, cellulosics, ethylene oxide modified phenols, and ethylene oxide/propylene oxide polymers. While the non-ionic technique is not sensitive to pH changes or ionic contamination, it has a major disadvantage for many applications in that the final product is water sensitive. Thus, if used in ink applications or the like, the pigment will tend to smear upon exposure to moisture.

In the ionic technique, the pigment particles are stabilized by a polymer of an ion containing monomer, such as neutralized acrylic, maleic, or vinyl sulfonic acid. The polymer provides stabilization through a charged double layer mechanism whereby ionic repulsion hinders the particles from flocculation. Since the neutralizing component tends to evaporate after application, the polymer then has reduced water solubility and the final product is not water sensitive.

Ideally, a polymer dispersant that provides both steric and charged double layer stabilization forces would make a much more robust pigment dispersion. Polymer dispersants having both random and block structures have been disclosed for this purpose. For example, U.S. Pat. No. 4,597,794 to Canon proposes an aqueous ink dispersion for ink jet printers in which a pigment is dispersed by a polymer having ionic hydrophilic segments and aromatic hydrophobic segments that adhere to the pigment surface. U.S. Pat. No. 5,085,698 to Ma et al. discloses the use of AB or BAB structured block polymers as pigment dispersants. While the random polymer dispersants can be prepared readily by conventional polymerization techniques, the structured block polymer dispersants generally offer improved dispersion stability. However, the structured block polymers usually require a more elaborate synthesis plan, more demanding reaction conditions, and high raw materials purity, as in the case of anionic polymerization and group transfer polymerization. A more convenient polymerization process, whereby desired structure may readily be built into the polymer, is desired for more advanced high quality dispersion applications such as ink jet printers.

Ink jet printing is a non-impact printing process wherein a digital signal produces ink droplets on media substrates, such as paper or transparency films. In thermal ink jet printing, resistive heating is used to vaporize the ink, which is expelled through an orifice in the ink jet printhead toward the substrate. This process is known as firing, in which water is vaporized by the heat, causing a very rapid and drastic local compositional change and temperature rise. This occurs repeatedly at high frequency during the life of the printhead. Further, in the orifice areas, the ink composition can drastically change from water-rich to solvent-rich due to evaporation of water. This tends to cause the pigment particles to flocculate around the orifice in the printhead, eventually leading to plugging of the orifice. Particle flocculation thus will cause misdirection of the ink drop, or prevent the drop to eject at all in extreme cases.

In conventional coating applications, many additives of organic nature are used to impart the desired physical properties for the final use. Examples include polymer binders, thickeners, thixotropic agents, coating aids, etc. During the drying process, these components are concentrated. The pigment dispersion needs to accommodate such changes in order to maintain the uniformity and color quality for the final coatings.

Accordingly, the need exists for dispersants which can be prepared by a convenient and inexpensive polymerization process, and will provide improved dispersion stability for improved quality for applications such as thermal ink jet printers.

SUMMARY OF THE INVENTION

The invention provides a dispersion having excellent stability, the dispersion containing an aqueous carrier medium, a particulate solid, and a cyclopolymer dispersant consisting essentially of at least one cyclopolymer having the formula:

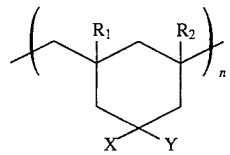

with the proviso that either (i) $R_1$ and $R_2$ are hydrophobic groups, and X and Y are hydrophilic groups, or (ii) $R_1$ and $R_2$ are hydrophilic groups, and X and Y are hydrophobic groups. The dispersions have broad compatibility with water miscible organic cosolvents, aqueous additives such as thickeners, latex emulsions, and the like. In a preferred embodiment, the particulate solid is a pigment and the resulting dispersion is employed as an ink particularly adapted for use in a thermal ink jet printer.

DETAILED DESCRIPTION OF THE INVENTION

The dispersions of this invention have excellent stability, and are particularly suited for use as aqueous ink jet ink compositions for ink jet printers in general, and thermal ink jet printers in particular. The inks may be adapted to the requirements of a particular ink jet printer to provide a balance of light stability, smear resistance, viscosity, surface tension, optical density, and crust resistance.

Aqueous Carrier Medium

The aqueous carrier medium is water or a mixture of water and at least one water soluble and/or water-dispersable organic component. Deionized water is commonly used. The organic component may be an organic solvent, polymeric binder, thickener, thixotropic agent, coating aid or other component conventionally used to adapt the dispersion to its intended application.

For ink jet inks, the aqueous carrier medium is typically a mixture of water and at least one water-soluble organic solvent. Representative examples of water-soluble organic solvents are disclosed in U.S. Pat. No. 5,085,698. Selection of a suitable mixture of water and water soluble organic solvent depends upon requirements of the specific application, such as desired surface tension and viscosity, the selected pigment, drying time of the pigmented coating or ink jet ink, and the type of media substrate onto which the coating or ink will be printed. A mixture of diethylene glycol and deionized water is preferred as the aqueous carrier medium for ink jet inks, with the composition typically containing between 30% and 95% (preferably 60% to 95%) water by weight, based on the total weight of the aqueous carrier medium.

Particulate Solids

The particulate solid may be a pigment, colloidal silver halide, metallic flake, a herbicide, an insecticide, or biomaterial such as a drug, or other solid depending upon the particular application of the dispersion. For example, if the intended use is in an ink or a paint, the particulate solid is a pigment or a mixture of two or more pigments. The term "pigment" as used herein means a colorant that is insoluble in the aqueous carrier medium.

Most particulate solids have functional groups on their surface, which are capable of "binding" with "binding sites" on the hydrophobic side of the selected cyclopolymer as discussed hereinafter. For example, carbon black particles typically have chemisorbed oxygen complexes on their surfaces, which are primarily acidic in nature; namely, the surface will have carboxylic, quinonic, lactonic, or phenolic groups to varying degrees that depend on manufacturing conditions. These acidic groups on the pigment surface provide binding sites for dispersants with basic functions, such as amine groups. With other pigments having acidic surfaces or basic surfaces, which are equally useful in this invention, either the pigment itself contains functional groups or the pigment surfaces have been modified by compounds containing functional groups such as sulfonic, phosphoric, and carboxylic acid groups or amine type of basic groups. Furthermore, almost all of the organic color pigments and many of the surface treatment compounds have aromatic features in their structures, providing sites for additional aromatic interactions with the dispersant. Examples of pigments which may be used to form the composition include azo, anthraquinone, thioindigo, oxazine, quinacridone, lakes and toners of acidic dye stuffs or basic dye stuffs, copper phthalocyanine and its derivatives, and various mixtures and modifications thereof.

The particle size and density of the particulate solid, and viscosity of the aqueous carrier medium, will have an influence on the dispersion stability. Brownian motion of minute particles will help prevent the particles from flocculation and settling. While the selected particle size thus will vary with the selected cyclopolymer dispersant, particle density, and other requirements of the specific application, particles as large as 30 microns may be selected for some applications.

For ink jet ink applications, the pigment particles need to be sufficiently small to permit free flow of the ink through the ink jet printing device, especially at the ejecting nozzles that typically have a diameter ranging from 10 to 50 microns. In addition, it is also desirable to use small particles for maximum color strength and gloss. The range of useful particle size is typically 0.005 to 15 microns, preferably 0.005 to 1 micron.

Also in the case of pigments, the selected pigment may be used in dry or wet form. For example, pigments are usually manufactured in aqueous media and the resulting pigment is obtained as water wet presscake. In presscake form, the pigment is not aggregated to the extent that it is in dry form. Thus, pigments in water wet presscake form do not require as much deaggregation in the process of preparing the inks from dry pigments. Representative useful commercial dry and presscake pigments are disclosed in the aforementioned U.S. Pat. No. 5,085,698.

Fine particles of metal or metal oxides (such as copper, iron, steel, aluminum, silica, alumina, titania, and the like) also may be used to practice the invention and may find applications in the preparation of magnetic ink jet inks and other coating applications for the electronic industries. Disperse dyes, which are aqueous carrier medium insoluble colorants, may be dispersed using the cyclopolymer dispersants of the invention.

Cyclopolymer Dispersant

The cyclopolymer dispersant has a hydrophilic section containing groups soluble in the aqueous carrier medium, and a hydrophobic section that binds with the selected particulate solid. These two sections are situated on the opposite sides of the polymer backbone as depicted in the following formula:

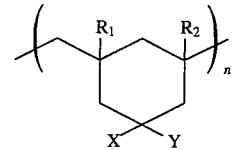

wherein (i) $R_1$ and $R_2$ are hydrophobic groups, and X and Y are hydrophilic groups, or (ii) $R_1$ and $R_2$ are hydrophilic groups, and X and Y are hydrophobic groups. The degree of polymerization (n) is such that the weight average molecular weight of the polymer is in the range of 1,000 to 50,000, and preferably less than 20,000. For ink jet ink applications, the weight average molecular weight typically is less than 10,000.

As stated above, $R_1$ and $R_2$ may be hydrophobic or hydrophilic, depending on the particular substituent that is selected. In general, $R_1$ and $R_2$ are independently selected from the group consisting of COOR, CN, C(O)$NHR_4$ and C(O)$NR_5R_6$ wherein R, $R_4$, $R_5$, and $R_6$ are independently selected from the group consisting of alkyl, substituted alkyl, aryl, or substituted aryl groups having 1 to 18 carbon atoms when the side containing $R_1$ and $R_2$ is used as the hydrophobic pigment binding side; or $R_1$ and $R_2$ may be independently selected from the group consisting of COOH, $COOR_7$, C(O)$NHR_8$, and C(O)$NR_9R_{10}$ wherein $R_7$, $R_8$, $R_9$ and $R_{10}$ are independently selected from the group consisting of alkyl, aryl, aralkyl, or alkylaryl group containing 1 to 30 carbon atoms and sufficient hydrophilic groups (e.g., hydroxy or ether groups) to render the side containing $R_1$ and $R_2$ as a whole hydrophilic, or preferably water soluble, when it is used as the hydrophilic side. A useful example of the hydrophilic groups for $R_7$ through $R_{10}$ includes $(CH_2CH_2O)_mH$ wherein m=1 to 15.

As stated above, X and Y are selected such that they are hydrophilic when $R_1$ and $R_2$ are hydrophobic, or hydrophobic when $R_1$ and $R_2$ are hydrophilic.

In general, when X and Y are hydrophobic they are independently selected from the group consisting of COOR, CN, $R_3CO$, $C(O)NHR_4$, and $C(O)NR_5R_6$ wherein R, $R_4$, $R_5$, and $R_6$ are defined as above and $R_3$ is an alkyl group containing 1 to 6 carbon atoms when the side containing X and Y is used as the hydrophobic pigment binding side. Or, when X and Y are hydrophilic they are independently selected from the group consisting of COOH, $PO_3H$, $SO_3H$, $COOR_7$, $C(O)NHR_8$, $C(O)NR_9R_{10}$, and $R_{11}CO$ wherein $R_7$, $R_8$, $R_9$, $R_{10}$ and $R_{11}$ are independently selected from the group consisting of alkyl, aryl, aralkyl or alkylaryl group containing 1 to 30 carbon atoms and sufficient hydrophilic groups (e.g., hydroxy or ether groups) to render the side containing X and Y as a whole hydrophilic or preferably water soluble when it is used as the hydrophilic side. A useful example of the hydrophilic groups for $R_7$ through $R_{11}$ includes $(CH_2CH_2O)_mH$ wherein m=1 to 15.

X and Y, together with the carbon atom to which they are attached, may form a carbocyclic or heterocyclic ring system. Suitable ring systems include a dimedone ring or 1,3-dioxan-4,6-dione ring, a barbituric acid ring, a 3-alkyl-isoxazol-5(4H)-ring or a 3-aryl-isoxazol-5(4H)-one ring. Substituents on the ring may be hydrophilic or hydrophobic in nature, as discussed above.

The term "substituted" alkyl or aryl as used herein means an alkyl or aryl group that contains one or more substituents that do not interfere with the polymerization process. Such substitutents may include alkyl, hydroxy, amino, ester, acid, acyloxy, amide, nitrile, halogen, haloalkyl, alkoxy, epoxide, nitro, thioether, sulfonyl ester, sulfonamide, silyloxy, alkyl-silyl.

To solubilize the hydrophilic side into the aqueous carrier medium, it may be necessary to make salts of the acid groups contained in this side. Salts of the acid groups are prepared by neutralizing with neutralizing agents. For example, the neutralizing agent may be an organic base such as amines; alkanol amines; pyridine; ammonium hydroxide or tetraalkyl ammonium hydroxide; an alkali metal hydroxide such as potassium, sodium or lithium hydroxide; carbonates, such potassium carbonate; and bicarbonates, such as potassium bicarbonate.

As mentioned above, the hydrophobic side of the cyclopolymer has "binding sites" that bind with the particulate solid. By "binding" it is meant that physical attraction is achieved between the particulate solid and cyclopolymer dispersant, generally without permanent chemical bonding. A first way that this binding may occur is through hydrophobic interactions wherein the cyclopolymer has substituents that are the same as those contained in or on the surface of the particulate solid. Pigment particles, for example, may be pretreated with substances which render the surface hydrophobic. The hydrophobic side of the cyclopolymer can bind to such surface through hydrophobic interactions.

A second way in which a cyclopolymer can bind to a solid particulate is through aromatic interactions. If the particulate solid contains aromatic or aromatic-like groups, or if its surface has been pretreated with an aromatic substance, then the aromatic groups in the hydrophobic side can further improve the binding force to the solid particulate.

A third way in which a cyclopolymer can bind to a particulate solid is through ionic bonds. For example, a solid particulate containing sulfonic acid groups can bind strongly to a cyclopolymer in which hydrophobic pigment binding side of the polymer contains amine groups. Similarly, a pigment containing quaternary ammonium groups can bind to a cyclopolymer through acid groups.

Covalent bonding provides a fourth, and especially strong, mode of binding a cyclopolymer dispersant to a particulate solid. For example, a particulate solid with carboxylic groups will react with a polymer which contains epoxy groups to form ester linkages. Thus, a cyclopolymer tailored to contain glycidyl methacrylate groups in the hydrophobic side will form permanent chemical links to a carboxylic acid-containing particulate solid.

The cyclopolymers can be easily prepared by techniques familiar to those skilled in the art, for example free radical polymerization. The molecular weight readily may be controlled by techniques well known in the art, such as the use of chain transfer agents, choice of polymerization solvent and temperature, amount of polymerization initiator, etc. They are prepared from 4,4-disubstituted 1,6-dienes of the following formula:

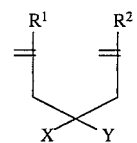

wherein $R_1$, $R_2$, X, and Y are defined as those corresponding groups in the polymers structure above. These disubstituted dienes may be synthesized by reacting a compound $X-CH_2-Y$ with two or more molar equivalents of a compound $H_2C=C(R_1)CH_2A$ in the presence of an organic or inorganic base, wherein A is a substituent that is removed during the reaction, such as a halide group. In this case, the diene contains two identical R groups (i.e., $R_1$ and $R_2$ are the same). Alternatively, compound $X-CH_2-Y$ may be reacted with one molar equivalent of the compound $H_2C=C(R_1)CH_2A$, followed by reaction with one molar equivalent of the compound $H_2C=C(R_2)CH_2A$, in the presence of an organic or inorganic base, to form a diene having different R groups.

The 4,4-disubstituted 1,6-diene monomers may be copolymerized with a minor amount of other types of monomers to modify the physical properties such as glass transition temperature (Tg) or the hydrophobicity/hydrophilicity balance for optimal dispersing properties of the polymer. Either hydrophobic or hydrophilic monomers may be used. Useful monomers may include for example acrylates, methacrylates, vinylaromatics, and acrylamides. Examples of such monomers are acrylic acid, methacrylic acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, δ-methylstyrene, vinylpyridine, N-vinylpyrrolidone, vinyl carbazole, vinyldene halide, and acrylonitrile.

Additives

Depending on the requirements for the intended application, various types of additives can be used to modify the properties of these solid particulate dispersions. Examples include organic cosolvents, coalescing agents, polymeric binders including the water soluble polymers and the water dispersable latex emulsions, thickeners, thixotropic agents, surfactants, coating aids, biocides, sequestering agents, etc.

When used in ink jet ink applications, the aqueous dispersions may contain anionic, cationic, nonionic, or amphoteric surfactants in the amount of 0.01–5% and preferably 0.2–2%, based on the total weight of the ink. Biocides such as Dowicides® (Dow Chemical, Midland, Mich.), Nuosept® (Huls America, Inc., Piscataway, N.J.), Omidines® (Olin Corp., Cheshire, Conn.), Nopcocides® (Henkel Corp., Ambler, Pa), Troysans® (Troy Chemical Corp., Newark, N.J.), and sodium benzoate; sequestering agents such as EDTA; and other known additives, such as humectants, viscosity modifiers and other polymers may also be added to improve various properties of the ink compositions.

The dispersion of aqueous carrier medium, particulate solid, and cyclopolymer dispersant is prepared using conventional technique(s) known in the art. For example, a pigment dispersion may be prepared by premixing the selected pigment(s) and the polymer in water. The dispersion step may be accomplished in a horizontal mini mill, a ball mill, an attritor, or by passing the mixture through a plurality of nozzles within a liquid jet interaction chamber at a liquid pressure of at least 1000 psi to produce a uniform dispersion of the pigment particles in the aqueous carrier medium. It is generally desirable to make the pigmented ink jet ink in concentrated form, which is subsequently diluted with a suitable liquid to the appropriate concentration for use in the ink jet printing system. By dilution, the ink is adjusted to the desired viscosity, color, hue, saturation density, and print area coverage for the particular application.

The preferred formulation in an ink jet ink composition is:

(a) aqueous carrier medium present in the amount of approximately 70% to 96%, preferably approximately 80% to 96, based on total weight of the ink when an organic pigment is selected; and approximately 25% to 96%, preferably approximately 70% to 96% when an inorganic pigment is selected;

(b) pigments present in the amount of up to approximately 30% pigment by weight for organic pigments, but generally in the range of approximately 0.1 to 15%, and preferably approximately 0.1 to 8%, by weight of the total ink composition. With inorganic pigments (which have higher specific gravities), higher concentrations are employed, and they may be as high as 75% in some cases;

(c) cyclopolymer present in the amount of approximately 0.1 to 30% by weight of the total ink composition, preferably in the range of approximately 0.1 to 8% by weight of the total ink composition.

Many ink performance features such as the drop velocity, separation length of the droplets, drop size, and stream stability are greatly affected by the surface tension and the viscosity of the ink. Pigmented ink jet inks suitable for use with ink jet printing systems should have a surface tension in the range of about 20 dyne/cm to about 70 dyne/cm and, more preferably, in the range of 30 dyne/cm to about 70 dyne/cm at 20° C. Acceptable viscosities are no greater than 20 cP, and preferably in the range of about 1.0 cP to about 10 cP at 20° C.

Industrial Applicability

The dispersions of this invention may be designed to provide excellent stability for organic and inorganic solids in aqueous media or mixed aqueous-organic media. The dispersions are particularly useful for coating applications such as paints and color films for imaging applications. They are also very useful for various types of inks.

EXAMPLES

This invention will now be further illustrated, but not limited, by the following examples.

Procedure 1

2,6-dibenzyloxycarbonyl-4,4-di-(t-butoxycarbonyl)1,6-heptadiene monomer was prepared using the following procedure:

To a cooled suspension of sodium hydride (5.12 g, 0.17 mol. dispersion in oil about 80% grade) in acetonitrile (300 mL), was added di-t-butyl malonate (14.78 g, 0.0684 mol). The resulting mixture was stirred at 4° C. for 15 minutes before a solution of benzyl 2-(bromomethyl)propenoate (34.9 g, 0. 137 mol) in acetonitrile (100 mL) was added. Benzyl 2-(bromomethyl)propenoate was obtained from the bromination reaction of the Bayliss-Hillman reaction product which was prepared with benzyl acrylate and paraformaldehyde in the presence of DABCO (1,4-diazabicyclo [2.2.2]octane). ($^1$H-NMR (CDCl$_3$) δ (ppm): 4.20 (s, 2H); 5.25 (s, 2H); 6.00 (s, 1H); 6.40 (s, 1H); and 7.40 (br. s, 5H)). The reaction mixture was then stirred at room temperature for 2 hours. Saturated sodium chloride solution (200 mL) was added and the mixture was extracted three times with diethyl ether (600 mL in total). The combined organic phase was washed with water, then brine. After drying over anydrous sodium sulfate, filtration and evaporation to dryness, it was chromatographed in a silica gel column (Merck 60, 70–230 mesh; 10% diethyl ether in petroleum spirit as eluent) to give the title compound (16.9 g, 44% yield) as a viscous colorless liquid. $^1$H-NMR (CDCl$_3$) δ (ppm): 1.45 (s, 18H); 2.98 (s, 4H); 5.15 (s, 4) 5.75 (s, 2H); 6.30 (s, 2H); and 7.35 (br. s, 10H).

Procedure 2

A cyclopolymer was prepared from 2,6-dibenzyloxycarbonyl-4,4-di-(t-butoxycarbonyl)-1,6-heptadiene monomer using the following procedure. The resulting polymer has hydrophilic groups (carboxylic acid) and hydrophobic aromatic groups (benzyl ester) on the opposite sides of the cyclohexane polymer backbone. It was prepared by free radical cyclopolymerization of the monomer, followed by hydrolysis reaction to convert the t-butoxycarbonyl groups to the carboxylic acid groups.

The monomer, 2,6-dibenzyloxycarbonyl-4,4-di(t-butoxycarbonyl)-1,6-heptadiene (15.4 g, 27.2 mol), and initiator α, α'-azobisisobutyronitrile (AIBN) (223 mg, 1.36 mol, 5% molar) were dissolved in o-xylene (270 mL). The mixture was degassed three times under vacuum (0.005–0.001 mm Hg) in a Young vessel. It was heated at 60° C. for 20 hours, followed by additional 2 hours at 90° C. After cooling, the polymer was precipitated with methanol and filtered to give 10.4 g (67% isolated yield) of a white powder. GPC (polystyrene as the standard): Mn=6064; Mw=12773; Mw/Mn=2.10.

The cyclopolymer (10.0 g) was then mixed with formic acid (70 mL) in dichloromethane (140 mL). The solution was refluxed for 18 hours. After cooling, the hydrolyzed product (7.82 g, 98% isolated yield) was isolated. $^1$H-NMR (Acetone-d6) showed complete loss of t-butyl group.

The cyclopolymer (7.22 g) was dissolved with potassium hydroxide (3.08 g, 46.6% solution) in deionized water (69.2 g) to give a clear 9.0% neutralized cyclopolymer solution.

Procedure 3

A pigment dispersion was prepared using a cyclopolymer prepared in Procedure 2 as follows:

| Ingredient | Amount (parts by weight) |
| --- | --- |
| FW18, Carbon black pigment (Degussa Corp. Allendale, NJ 07041) | 16 |
| Neutralized cyclopolymer solution, (9% solution) | 79.5 |
| Deionized water | 63.8 |
| Total | 159.3 |

The above mentioned components were premixed in a plastic beaker by mechanical stirring until no lumps or dry clumps were visible. The mixture was dispersed in a microfluidizer (Microfluidics Corp., Watham, Mass.) by passing it through the interaction chamber 5 times under a liquid pressure of about 7,000 psi. The resulting pigment dispersion had 10% pigment concentration with an average particle size of 120 nm as determined by Brookhaven BI-90 particle sizer. The dispersion was filtered through a 1 micron high efficiency filter bag (3M Filtration Products, St. Paul, Minn. 55144-1000). The final pH was 10.8.

Ink Test

The pigment dispersion concentrate (10%) from Procedure 3 was letdown with a vehicle solution to give the following composition.

| Ingredient | Amount (parts by weight) |
| --- | --- |
| Carbon Black, FW18, (Degussa Corp., Allendale, NJ) | 4.0 |
| Cyclopolymer from Procedure 2 | 1.8 |
| 2-Pyrrolidone (Aldrich Chemical Co., Milwaukee, WI) | 3.0 |
| N-Methylpyrrolidone (Aldrich Chemical Co., Milwaukee, WI) | 2.0 |
| Liponic EG-1 (Lipo Chemicals, Inc., Patterson, NJ) | 3.0 |
| Zonyl FSA (DuPont Co., Wilmington, DE) | 0.05 |
| Deionized water | 82.2 |

The ink was filled into a thermal ink jet pen and printed with a Hewlett Packard DeskJet ink jet printer (Hewlett Packard Co., Palo Alto, Calif.) on Gilbert bond paper (25% cotton, Mead Co., Dayton, Ohio). It printed smoothly and the print had an extremely high optical density of 1.58 and sharp edges. The print was waterfast immediately after drying.

The ink stability was determined by measuring the particle size change by Brookhaven BI-90 particle sizer (Brookhaven Instrument Corp., Holtsville, N.Y. 11742) after the ink sample had been subjected to 4 temperature cycles, each consisting of 4 hours at −20° C. and 4 hours at 70° C. The above ink showed no significant change.

What is claimed is:

1. A dispersion comprising an aqueous carrier medium, a particulate solid, and a cyclopolymer dispersant consisting essentially of at least one cyclopolymer having the formula:

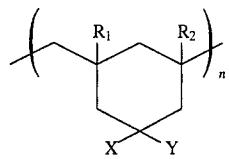

with the proviso that either (i) $R_1$ and $R_2$ are hydrophobic groups, and X and Y are hydrophilic groups, or (ii) $R_1$ and $R_2$ are hydrophilic groups, and X and Y are hydrophobic groups; and n is selected such that the weight average molecular weight of the cyclopolymer is in the range of 1,000 to 50,000.

2. The dispersion of claim 1 wherein $R_1$ and $R_2$ are hydrophobic groups independently selected from the groups consisting of COOR, CN, C(O)NHR$_4$ and C(O)NR$_5$R$_6$ wherein R, $R_4$, $R_5$, and $R_6$ are independently selected from the group consisting of alkyl, substituted alkyl, aryl, or substituted aryl groups having 1 to 18 carbon atoms, wherein the substituted group is a substituent that does not interfere with the polymerization process.

3. The dispersion of claim 2 wherein X and Y are hydrophilic groups independently selected from the group consisting of COOH, PO$_3$H, SO$_3$H, COOR$_7$, C(O)NHR$_8$, C(O)NR$_9$R$_{10}$, and R$_{11}$CO wherein R$_7$, R$_8$, R$_9$, R$_{10}$ and R$_{11}$ are independently selected from the group consisting of alkyl, aryl, aralkyl or alkylaryl group containing 1 to 30 carbon atoms and sufficient hydrophilic groups to render X and Y as a whole hydrophilic.

4. The dispersion of claim 1 wherein $R_1$ and $R_2$ are hydrophilic groups independently selected from the group consisting of COOH, COOR$_7$, C(O)NHR$_8$, and C(O)NR$_9$R$_{10}$ wherein R$_7$, R$_8$, R$_9$ and R10 are independently selected from the group consisting of alkyl, aryl, aralkyl or alkylaryl group containing 1 to 30 carbon atoms and sufficient hydrophilic groups to render the $R_1$ and $R_2$ as a whole hydrophilic.

5. The dispersion of claim 4 wherein X and Y are hydrophobic groups independently selected from the group consisting of COOR, CN, R$_3$CO, C(O)NHR$_4$, and C(O)NR$_5$R$_6$ wherein R, $R_4$, $R_5$, and $R_6$ are independently selected from the group consisting of alkyl, substituted alkyl, aryl, or substituted aryl groups having 1 to 18 carbon atoms and $R_3$ is an alkyl group containing 1 to 6 carbon atoms, wherein the substituted group is a substituent that does not interfere with the polymerization process.

6. The dispersion of claim 1 wherein said particulate solid is a pigment.

7. The dispersion of claim 6 wherein said pigment has a particle size in the range of 0.005 to 15 microns.

8. The dispersion of claim 1 wherein said dispersion is an ink jet ink containing 70 to 96% aqueous carrier medium, up to 30% by weight of an organic pigment, up to 75% by weight of an inorganic pigment, and 0.1 to 30% by weight cyciopolymer dispersant.

9. The dispersion of claim 1 containing at least one additive selected from the group consisting of organic solvents, polymeric binders, water-soluble polymers, water-dispersible latex emulsions, thickeners, coalescing agents, surfactants, biocides, sequestering agents, thixotropic agents and coating aids.

* * * * *